United States Patent
Colman et al.

(10) Patent No.: US 11,026,595 B2
(45) Date of Patent: Jun. 8, 2021

(54) FEATURE TREND DISPLAY

(71) Applicant: ORIDION MEDICAL 1987 LTD., Jerusalem (IL)

(72) Inventors: Joshua Lewis Colman, Jerusalem (IL); Michal Ronen, Bet-Elazari (IL)

(73) Assignee: ORIDION MEDICAL 1987 LTD., Jerusalem (IL)

( * ) Notice: Subject to any disclaimer, the term of this patent is extended or adjusted under 35 U.S.C. 154(b) by 195 days.

(21) Appl. No.: 14/171,128

(22) Filed: Feb. 3, 2014

(65) Prior Publication Data
US 2015/0216447 A1  Aug. 6, 2015

(51) Int. Cl.
*A61B 5/083* (2006.01)
*A61B 5/08* (2006.01)
*A61B 5/00* (2006.01)

(52) U.S. Cl.
CPC ............ *A61B 5/082* (2013.01); *A61B 5/0836* (2013.01); *A61B 5/7235* (2013.01); *A61B 5/7275* (2013.01); *A61B 5/742* (2013.01); *A61B 5/743* (2013.01)

(58) Field of Classification Search
CPC ....... A61B 5/082; A61B 5/7275; A61B 5/742; A61B 5/0836; A61B 5/7235; A61B 5/743
See application file for complete search history.

(56) References Cited

U.S. PATENT DOCUMENTS

| | | | |
|---|---|---|---|
| 5,598,508 A * | 1/1997 | Goldman | A61B 5/0803 706/20 |
| 5,751,911 A | 5/1998 | Goldman | |
| 8,000,937 B2 | 8/2011 | Lingbo | |
| 9,770,191 B2 * | 9/2017 | Colman | A61B 5/0836 |
| 10,178,962 B2 * | 1/2019 | Colman | A61B 5/08 |
| 2002/0082511 A1 * | 6/2002 | Carlebach | A61B 5/0836 600/529 |
| 2002/0177793 A1 | 11/2002 | Sherman et al. | |
| 2003/0073919 A1 * | 4/2003 | Hampton | A61B 5/0836 600/532 |
| 2006/0155206 A1 | 7/2006 | Lynn | |
| 2007/0191697 A1 | 8/2007 | Lynn et al. | |
| 2008/0039735 A1 * | 2/2008 | Hickerson | A61B 5/7445 600/532 |
| 2009/0149723 A1 | 6/2009 | Krauss et al. | |
| 2011/0040713 A1 * | 2/2011 | Colman | A61B 5/0836 706/16 |
| 2012/0016251 A1 * | 1/2012 | Zhang | A61B 5/0402 600/532 |
| 2012/0105485 A1 | 5/2012 | Colman | |
| 2012/0302910 A1 | 11/2012 | Freeman et al. | |

(Continued)

FOREIGN PATENT DOCUMENTS

WO  2011/154948  12/2011

OTHER PUBLICATIONS

Einav et al., (2011) Mathematical modeling for prediction of survival from resuscitation based on computerized continuous capnography: proof of concept. Acad Emerg Med 18(5): pp. 468-475.

(Continued)

*Primary Examiner* — Navin Natnithithadha
(74) *Attorney, Agent, or Firm* — Cantor Colburn LLP

(57) ABSTRACT

Provided are systems and method for identifying, generating and displaying a trend of one or more medical waveform related features.

17 Claims, 3 Drawing Sheets

(56) References Cited

U.S. PATENT DOCUMENTS

| | | |
|---|---|---|
| 2013/0324873 A1 | 12/2013 | Babaeizadeh et al. |
| 2016/0128626 A1 | 5/2016 | Johnson et al. |
| 2016/0287170 A1 | 10/2016 | Ronen et al. |
| 2018/0116554 A1* | 5/2018 | Colman .................. A61B 5/08 |

OTHER PUBLICATIONS

International Application No. PCT/IL2015/050031 Written Opinion and International Search Report dated Mar. 27, 2015, 8 pages.

\* cited by examiner

FEATURE TREND DISPLAY

TECHNICAL FIELD

The present disclosure generally relates to medical monitoring systems and methods of using the same.

BACKGROUND

Medical monitoring devices are routinely used in various medical settings to obtain or measure medical parameters relating to a patient's medical condition. Many medical parameters related to a patient being monitored and measured can be presented or described by a continuous and recurring train of waveforms. Such waveforms may include, for example, $CO_2$ concentration or breathe flow rate of a patient's breath measured over time; an ECG signal measured over time, and the like. Such waveforms are produced from the cyclic breathing patterns or heart contractions (beats), respectively. Each waveform have a characteristics shape and dimensions that are a direct result of the patients physiology and state at the time of the measurement, and hence are indicative and informative to the patients' medical status, either as single waveforms or a sequential reoccurrence of waveforms over time.

Trending medical waveform parameters, such as, for example, End tidal $CO_2$ (Et$CO_2$, the maximum $CO_2$, concentration measured in a breath cycle), Respiration Rate (RR), and the like, are calculated and displayed on relevant monitors such as Capnographs, using dedicated trend screens, where, for example, the x axis is time, and y axis is the measured value (for example, the Et$CO_2$ or RR value). Such conventional trends relate traditionally to parameters (such as amplitude of the waveform or rate), which are extracted or calculated directly from the received waveform and are generally constructed using two dimensional depictions of these parameters (for example, amplitude vs. time).

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other advantages or improvements.

According to some embodiments, there are provided methods and systems for the determination, identification and extraction of various features (parameters) of medically, time resolved waveforms, analysis thereof and their trend presentation over time.

According to some embodiments, the methods and systems provided herein may be used for the depiction and calculation of a trend of waveform related features/parameters which may be extracted from a train of medical waveforms, thereby allowing the detection or indication of the condition and status of a given patient, being monitored. In some embodiments, the methods and systems may further be used to identify patterns of the waveform related parameters trends and to correlate between a pattern and a medical status of the patient.

In some embodiments, various pattern recognition algorithms may be performed upon the trends to determine if a pattern can be identified and/or a correlation of the identified pattern to a given medical situation can be made. In some embodiments the methods and systems disclosed herein further take use of various calculation tools, such as pattern finding algorithms and other tools for extracting, marking, zoom in, detecting and/or identifying known or new patient health related conditions, as indicated by the waveform feature related trends.

Thus, the methods and systems disclosed herein advantageously provide the health care provider with an efficient, accurate and time saving system for analyzing and evaluating the medical condition of the patient, such as his respiratory status, cardiac status, and the like.

Each waveform have a characteristics shape and dimensions that are a direct result of the patients physiology and state at the time of the measurement, and hence are indicative and informative to the patients' medical status. Using the systems and methods disclosed herein, a more accurate assessment of the medical status of the patient is reliably accessed, by identifying, determining and providing a trend analysis over time of various waveform related parameters. By utilizing the systems and methods disclosed herein, the health care provider can better sense what parameters are recurring and dominant, which parameters are changing or erratic in nature, which parameters are producing patterns over time, and the like. This additional information provided by the systems and methods disclosed herein advantageously provide a far more reliable and accurate assessment of the patients' status as opposed to analyzing a single waveform or several sequential waveforms individually (as is generally observed on a standard monitor screen of a medical monitoring device).

Additionally, as opposed to conventional trends, which are traditionally related to parameters that are extracted or calculated directly from the received waveform (parameters such as, amplitude or rate) and are generally constructed using two dimensional depictions of these parameters (for example, amplitude vs. time), the trends provided by the methods and systems disclosed herein are of various waveforms related parameters which are attributed, calculated and/or extracted from various elements of the waveform (such as the shape of the waveform) and not merely of changes to the waveform overtime. By providing such trend data of those waveform related parameter, such as characteristics of the waveforms, their shapes, and interrelations there between, in two or more dimensions provides an enhanced tool for evaluating, indicating and diagnosing a patient status.

Further, with respect to displaying waveform related parameters that are related to the shape of the waveform and/or changes thereto, the methods and systems provided herein advantageously provide the health care provider with detection and analysis of information buried" in the waveform shape, which is not readily available otherwise and cannot be simply derived from the display of the waveform itself. The methods and systems further advantageously provide the health care provider with additional valuable information regarding the patient status, which are derived from the waveform such as, detection of patterns, dominance or changes over time and the like, which otherwise cannot be simply detected or identified.

According to some embodiments, there is provided a medical monitoring system for identifying a trend of waveform related features, the system comprising: a medical monitoring device configured to produce waveforms of a measured medical parameter of a patient; a computing unit configured to identify and extract one or more features related to the waveforms produced by said device, and produce a trend of said one or more waveform related features; and a display unit configured to display the trend of the one or more waveform related features.

According to some embodiments, the medical parameter of the patient is $CO_2$ in exhaled breath.

According to some embodiments, the waveform is a $CO_2$ related waveform.

According to some embodiments, the one or more waveform related features are selected from shape factors and scale factors. In some embodiments, the shape factors are selected from: up-rising slope of a CO2 waveform; the extent of the up-rising slope, the shape of the up-rising slope, the down-stroke slope of a CO2 waveform, the extent of the down stroke slope, the shape of the down stroke slope, and combinations thereof. According to some embodiments, the scale factors are selected from: width of the waveform, time between sections of the waveform, amplitude, and combinations thereof.

In some embodiments, the $CO_2$ waveform related feature is selected from: EtCO$_2$, changes in EtCO$_2$, a slope of the increase in the $CO_2$ concentration, a change in a slope of the increase in the $CO_2$ concentration, time to rise to a predetermined percentage of a maximum value of $CO_2$ concentration, a change in time to rise to a predetermined percentage of a maximum value of $CO_2$ concentration, an angle of rise to a predetermined percentage of a maximum value of $CO_2$ concentration, a change in an angle of rise to a predetermined percentage of a maximum value of $CO_2$ concentration, breath to breath correlation, a change in breath to breath correlation, a $CO_2$ duty cycle, a change in $CO_2$ duty cycle, minute ventilation, a change in minute ventilation, and combinations thereof.

In some embodiments, the computing unit is further configured to apply a pattern recognition algorithm to identify recurring pattern within the trend of the waveform related features.

In some embodiments, the trend of the waveform related feature is indicative of the health condition of the patient.

In some embodiments, the display unit is configured to display the trend of more than one waveform related feature in one trend display.

According to some embodiments, the medical monitoring device is a capnograph.

According to some embodiments, there is provided a method for identifying a trend of a medical waveform related feature, the method comprising: a) extracting one or more features of the waveform; b) detecting the change of the one or more features over time to create a trend of the one or more features of the trend; and c) displaying the identified trend.

In some embodiments, the medical waveform in the method is a CO2 related waveform. In some embodiments, the one or more waveform related features are selected from shape factors and scale factors. In some embodiments, the shape factors are selected from up-rising slope of a CO2 waveform; the extent of the up-rising slope, the shape of the up-rising slope, the down-stroke slope of a CO2 waveform, the extent of the down stroke slope, the shape of the down stroke slope, and combinations thereof. In further embodiments, the scale factors are selected from width of the waveform, time between sections of the waveform, amplitude, and combinations thereof. In some embodiments, the CO2 waveform related feature is selected from: EtCO2, changes in EtCO2, a slope of the increase in the CO2 concentration, a change in a slope of the increase in the CO2 concentration, time to rise to a predetermined percentage of a maximum value of CO2 concentration, a change in time to rise to a predetermined percentage of a maximum value of CO2 concentration, an angle of rise to a predetermined percentage of a maximum value of CO2 concentration, a change in an angle of rise to a predetermined percentage of a maximum value of CO2 concentration, breath to breath correlation, a change in breath to breath correlation, a CO2 duty cycle, a change in CO2 duty cycle, minute ventilation, a change in minute ventilation, and combinations thereof.

In some embodiments, the method may further comprise a step of identifying a recurring pattern within the trend of the waveform related features.

In further embodiments the pattern is identified by one or more of: neural networks, Support vector machines, decision trees, k-nearest-neighbor, radial-basis networks, Raves classifier, Linear discriminant analysis, Linear regression, Hidden Markov Models, K-means clustering, mixture models, Bayesian networks, fuzzy logic, ID3 and C4.5 algorithms, and combinations thereof.

In some embodiments, the method further comprises displaying the trend of more than one waveform related feature in a single trend display.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

In addition to the exemplary aspects and embodiments described above, further aspects and embodiments will become apparent by reference to the figures and by study of the following detailed descriptions.

DETAILED DESCRIPTION

Figure 1:
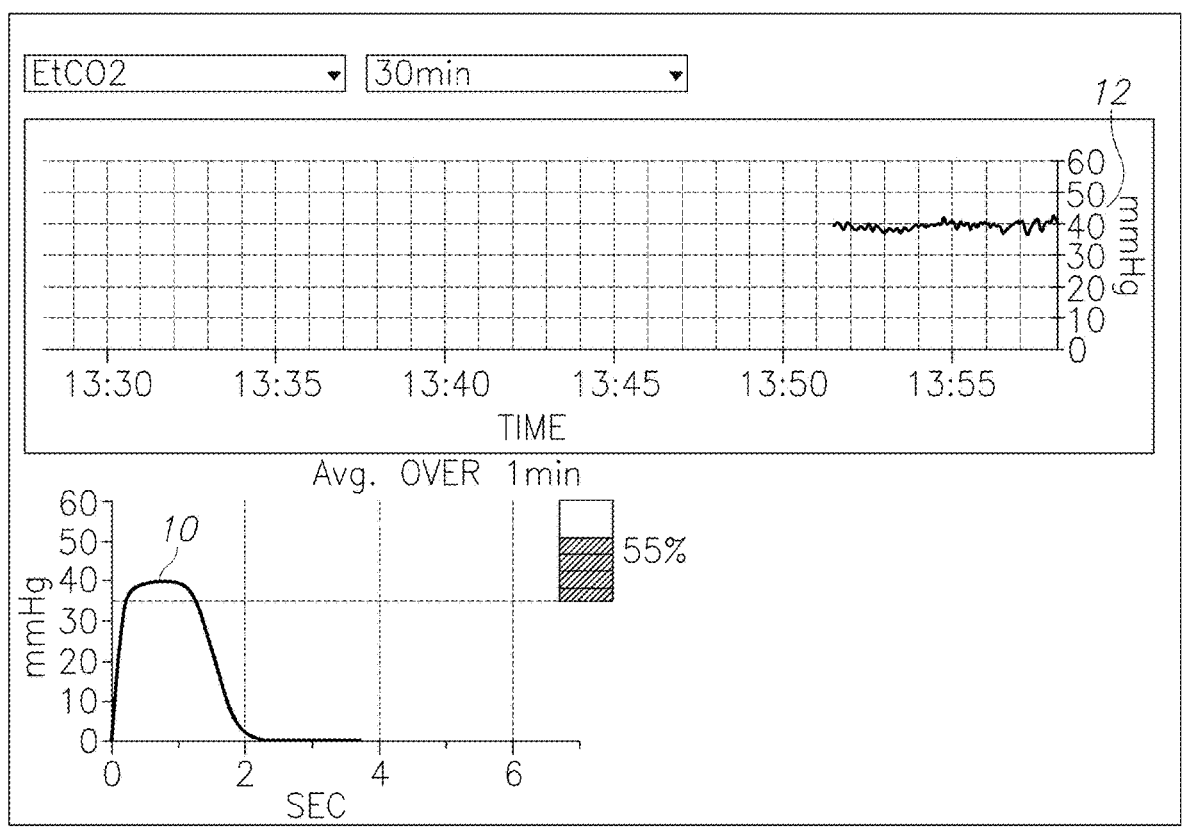
FIG. 1—a schematic representation of an exemplary display of a trend of a respiration waveform related feature and a representative waveform, according to some embodiments.

In the following description, various aspects of the invention will be described. For the purpose of explanation, specific configurations and details are set forth in order to provide a thorough understanding of the invention. However, it will also be apparent to one skilled in the art that the invention may be practiced without specific details being presented herein. Furthermore, well-known features may be omitted or simplified in order not to obscure the invention.

As referred to herein, the terms "user", "medical user", "health care provider" and "health care professional" may interchangeably be used. The terms may include any health care provider who may treat and/or attend to a patient. A user may include, for example, a nurse, respiratory therapist, physician, anesthesiologist, and the like. In some cases, a user may also include a patient.

As referred to herein, the terms "device", "monitoring device" and "medical device" may interchangeably be used.

As referred to herein, the terms "patient" and subject" may interchangeably be used and may relate to a subject being monitored by any monitoring device for any physical-condition related parameter and/or health related parameter.

As referred to herein, the terms ordinary, normal, typical, standard and common may interchangeably be used.

As referred to herein, the term "waveform" is directed to a recurring graphic shape which may be realized by measuring a physiological parameter of a subject over time, such as, for example, concentration of $CO_2$ in breath, flow rate of breath, electrocardiogram (ECG), pletyhsmograph, and the like. In some embodiments, a waveform is a medically, time resolved waveform. A waveform may have various characteristic parameters/features/factors that may be derived from the shape, dimension, rate or frequency, reoccurrences, and the like, and combinations thereof. In some embodiments, a feature extracted from the waveform is referred to herein as a "waveform related feature", "feature of the waveform", "waveform related parameter", "parameter related to the waveform" or "waveform related factor".

The term "Representative Waveform" is directed to a calculated single waveform that is produced by analyzing a set of waveforms and factors thereof, and defining a single waveform that is representative of the waveforms.

As referred to herein, the terms "waveform groups" or "waveform sets" relate to a sequential set of at least two waveforms.

As referred to herein, the terms "scaling factor(s)" or "scalar factor(s)" relate to measures of a waveform dimensions (such as, amplitude, width, time between sections of waveform and the like). In some embodiments, a scaling factor may be a waveform related feature.

As referred to herein, the term "shape factor(s)" relate to measures or characteristics related to the shape of the waveform (for example, slopes, curvatures, area under curve, and the like). In some embodiments, the shape factors may be a waveform related feature.

As referred to herein, the terms "rate factor(s)" or "frequency factor(s)" relate to measures of the waveform recurrence, the rate of change of the waveform, rate of change of the scaling or shape factors. In some embodiments, each of the rate factors may be a characteristic parameter/feature of the waveform.

As referred to herein, the term "pattern(s)": relates to any identified/determined pattern over time, which is recurring, known or unknown, that may be produced when graphically displaying any of the waveforms or waveforms related factors/parameters. In some embodiments, a pattern may be predefined. In some embodiments, a pattern may determined if it is clearly repeating itself for a given number of times (for example, 2-10 times), over a given period of time (for example, 30-1200 seconds). For example, a pattern is determined if it is clearly repeating itself at least twice over a given period of time As referred to herein, the term "$EtCO_2$" relates to End tidal $CO_2$. The $CO_2$ is exhaled out of the body and the concentration of the exhaled $CO_2$, also known as end tidal $CO_2$ ($EtCO_2$) is an approximate estimation of the alveolar $CO_2$ pressure and thus of the arterial levels of $CO_2$. The values of EtCO2 may be measured in units of pressure, such as, for example, mmHg.

As referred to herein, the term "breath cycle" includes the stages of exhalation and inhalation. The breath cycle may be derived from a $CO_2$ waveform which depicts the change in expired $CO_2$ Volume over time, ($EtCO_2$). During a breath cycle, the levels of $CO_2$ initially increase as a result of $CO_2$ release from the airways, from what is known as the "dead space", which is the space in which no gas exchange takes place. Then, the $CO_2$ rapidly reaches a plateau at high levels of $CO_2$, which corresponds to the release of $CO_2$ from the lungs, in the exhalation phase. A rapid decline in exhaled $CO_2$ proceeds the inhalation phase, characterized by absence/minute levels of $CO_2$.

According to some embodiments, the terms "calculated" and "computed" may interchangeably be used.

According to some embodiments, there is provided a method for identifying a trend of waveform related features, the method comprising extracting one or more features of the waveform, and detecting the change of the one or more features over time to create a trend of the one or more features of the trend; and displaying the identified trend.

According to some embodiments, there is provided a system for identifying and displaying a trend of waveform related features, the system comprises a medical monitoring device configured to produce a waveform of a medical parameter of a patient; a computing unit configured to identify and extract one or more features related to the waveform and produce a trend of said one or more waveform related features; and a display unit configured to display the trend of the one or more waveform related features.

According to some embodiments, the waveform is a medical waveform of a physiological parameter of a patient being monitored. In some embodiments, the waveform is obtained/measured by a medical device measuring and/or analyzing a medical parameter of the patient. In some embodiments, the medical parameter is respiration (for example, as measured by $CO_2$ concentration in exhaled breath), heart rate, and the like, or combinations thereof.

According to some embodiments, a medical waveform is a waveform related to respiration, and can be obtained by capnography. In capnography, a capnograph collects samples of a patient's breath, senses and calculates the real time $CO_2$ concentration (as partial $CO_2$ pressure) of the sample. The calculated $CO_2$ concentration over time is depicted on an appropriate display as a moving waveform (also referred to as capnogram). The resolution of the moving waveform and the sweep time are such that a user can identify breath cycles on the display. The information obtained in capnography may be used to determine a condition of a patient.

According to some embodiments, there is provided a system for identifying and displaying a trend of a respiration waveform related features, the system comprising a capnograph configured to produce a waveform of $CO_2$ concentration in exhaled breath of a patient over time; a computing unit (processor) configured to identify and extract one or more features related to the waveform and produce a trend of said one or more waveform related features; and a display unit configured to display the trend of the one or more waveform related features. In some embodiments, the system may further provide information regarding additional breath related parameters, such as, for example, breath rate, and further provide a trend thereof.

According to some embodiments, there is provided a method for identifying and displaying a trend of a respiration waveform related feature(s), the method comprising extracting one or more features of the waveform, and detecting the change of the one or more features over time to create a trend of the one or more features of the trend; and displaying the identified trend.

According to some embodiments, there is provided a method for use in a system for identifying and displaying a trend of medical waveform related features, the system comprises a medical monitoring device configured to produce a waveform of a medical parameter of a patient; a computing unit configured to identify and extract one or more features related to the waveform and produce a trend of said one or more waveform related features; and a display unit configured to display the trend of the one or more waveform related features.

According to some embodiments, there is provided a method used in a system for identifying and displaying a trend of a respiration waveform related features, the system comprising a capnograph configured to produce a waveform of $CO_2$ concentration in exhaled breath of a patient over time; a computing unit (processor) configured to identify and extract one or more features related to the waveform and produce a trend of said one or more waveform related features; and a display unit configured to display the trend of the one or more waveform related features.

According to some embodiments, a waveform can be characterized by two types of factors, namely shape factors and by scale factors. Shape factors characterize and/or describe the shape or pattern of the waveform. A shape factor may include, for example, parameters of a non-linear function describing an upstroke of the waveform. Scale factors are the waveform values and/or ratios, for example, height, width, width at half-height, duty cycle, or any other value or combination of values.

According to some embodiments, the waveform related features may be selected from scale factors and shape factors.

According to some embodiments, the medical waveform is a CO2 waveform. In some embodiments, the CO2 waveform may be obtained by a capnograph. In some embodiments, a typical, $CO_2$ waveform is a curve which represents the varying $CO_2$ levels throughout the respiratory cycle. In phase I, which represents the end of respiration, CO2 level is zero. Next, as exhalation begins, a sloped upstroke is observed (Phase II). Follows is a gradual rise (Phase III), a plateau having a peak just before a point which marks the end of exhalation. This is followed by a sharp down-stroke back to zero (inspiration, Phase IV), which is followed by a clean inspiration period.

According to some embodiments, a shape factor feature of a $CO_2$ waveform may be selected from, but not limited to: the up-rising slope of a $CO_2$ waveform; the extent of the slope, the shape of the slope, the down stroke slope, extent of the down stroke slope, the shape of the down stroke slope, and like.

In some embodiments, a trend of slope features of a waveform can be obtained by the systems and methods disclosed herein, by extracting such features from the waveform analyzing their occurrence and/or frequency and/or distribution over time to produce a trend of said features. By analyzing, producing and displaying the trend of these features, a reliable and enhanced means that can aid the health care provider in assessing or assisting in diagnosing the patient status (for example, severe, moderate, light or even differentiating between artifact and real) is obtained, since looking at any individual waveform, could not be used to indicate a patient condition nor severity.

According to some embodiments, a patient with asthma (or in some cases even a patient not having asthma) can have both "normal" and "sloped" waveforms. But looking at a trend of the waveforms features, their dominance; patterns thereof, a measure of slope extent and/or shape over time, provide stronger evidence and indication to the patient's condition and can be used to a greater advantage for monitoring the treatment of the patient.

According to some embodiments, a scale factor feature of the waveform may be selected from, but not limited to: amplitude, the variability of the amplitude, mean of the amplitude, dispersion of the amplitude, width of the waveform, the variability of the wave form, mean of the waveform, dispersion of the waveform, time between sections of the waveform, the variability of the time between sections of the waveform, mean of the time between sections of the waveform, dispersion of the time between sections of the waveform, Inhalation to Exhalation Ratio, variability of the Inhalation to Exhalation Ratio, mean of the Inhalation to Exhalation Ratio, dispersion of the Inhalation to Exhalation Ratio, and the like.

According to some embodiments, the $CO_2$ waveform related feature may be selected from, but not limited to: $EtCO_2$, changes in $EtCO_2$, a slope of the increase in the $CO_2$ concentration, a change in a slope of the increase in the $CO_2$ concentration, time to rise to a predetermined percentage of a maximum value of $CO_2$ concentration, a change in time to rise to a predetermined percentage of a maximum value of $CO_2$ concentration, an angle of rise to a predetermined percentage of a maximum value of $CO_2$ concentration, a change in an angle of rise to a predetermined percentage of a maximum value of $CO_2$ concentration, breath to breath correlation, a change in breath to breath correlation, a $CO_2$ duty cycle, a change in $CO_2$ duty cycle, minute ventilation, a change in minute ventilation, the I:E ratio and changes thereto, the variability of one or more of the $CO_2$ waveform related features; the measure of said variability; the correlation between two or more $CO_2$ waveform related features, the correlation between two or more $CO_2$ waveform related features and other breath related parameters, (for example, correlation of area under the curve (convolution) with breath flow rate), and the like, or any combination thereof. Each possibility is a separate embodiment.

According to some embodiments, the trend data of the waveform related features may be derived from a single waveform or a train of waveforms. In some embodiments, the trend data of the waveform related features may be derived from the shape factor or scale factor or rate factors that have been evaluated to be dominant over a given set of waveforms. In some embodiments, the trend data of the waveform related features may be derived from the shape factor or scale factor of a representative waveform.

According to some embodiments, the methods disclosed herein can further be used to correlate one or more of the trend features over time with additional medical parameters, such as, for example, but not limited to: blood pressure, medication, depth of sleep, desaturation, medication, and the like. In some embodiments, the clooected information may be used to better evaluate the condition of the patient and may be used to improve medical related decisions, such as, for example, with respect to weaning, sedation, and the like.

According to some embodiments, the methods and systems disclosed herein further provide for pattern recognition, by searching and detecting patterns of recurring events, which may be indicative of a given condition. Such pattern recognition can be used to detect known or unknown patterns with the trend data of the waveform related features. The pattern recognition may be performed by the processing unit. In some embodiments, the processing unit comprises an analyzing unit (an analyzer) configured to utilize a various algorithms to identify and/or calculate a pattern of the trend of the waveform related features.

In some embodiments, the pattern recognition can be used to detect known patterns or patterns that are less known but have been observed for the given patient class (for example, patient under a given condition or clinical environment or clinical procedure), or for the specific patient.

In some embodiments, the patterns identified can be defined according to established, known patterns (such as, for example, with respect to monitoring of respiration: Kossmaul breathing, Biot's respiration, Cluster breathing, Cheyne Stokes respiration, and the like). In some embodiments, the patterns identified can be defined in accordance with their identification in real time or off-line (i.e., not while the patient is being monitored and the waveform related features are analyzed and presented).

According to some embodiments, the patterns thus identified can be attributed to classes of patient's clinical or therapeutic status (for example, with respect to monitoring of respiration, if the patient is during weaning, if the patient is under SIMV ventilation mode, and the like).

According to some embodiments, the pattern identification, recognition and/or discovery can be performed by various supervised and unsupervised methods and algorithms, such as, for example, but not limited to: neural networks, Support vector machines, decision trees, k-nearest-neighbor, radial-basis networks, Raves classifier, Linear discriminant analysis, Linear regression, Hidden Markov Models, K-means clustering, mixture models, Bayesian networks, fuzzy logic, ID3 and C4.5 algorithms, and combinations thereof. Each possibility is a separate embodiment.

According to some embodiments, the system may further include a display unit (such as a monitor) configured to display the trend of the waveform related feature(s). In some embodiments, the display unit may display a trend of one or more waveform related parameters. When displaying the trend of more than one waveform related features, the displayed trends may be displayed simultaneously. The trends may be visually separated by shape (for example, columns, circles, dots, and the like); display pattern (for example, solid, empty, full, patterned); display color; display icons, and the like. In some embodiments, the presented trends may be further marked based on their physiological relevance. For example, with respect to respiration monitoring, trends of features which are indicative or related to obstructive or restrictive breathing; hyperventilation or hypoventilation; Cheyne stokes; and the like may, each be differentially presented in accordance with its respective physiological relevance. In some embodiments, the trend(s) may be displayed together with presentation of additional medical parameters, such as, for example, a medical waveform. In some embodiments, the display unit may further display any parameter useful for the health care provider in tracking the patient's breath and medical condition. In some embodiments, such parameters may be selected from, but not limited to: electrocardiogram, electroencephalogram, electrogastrogram, electromyogram, heart rate signals, pathological sounds, ultrasound, or any other suitable medical parameter. In some embodiments, the display unit may be integrally formed with the monitoring device. In some embodiments, the display unit may be functionally connected to the device.

According to some embodiments, the system may further include a user interface or a controller, that may allow the user to select the data to be displayed and/or to control various operating parameters. In some embodiments, the user may select which waveform related features are to be analyzed and/or trended. In some embodiments, the user may select which waveform related feature trends are displayed. In some embodiments, the user may select a time frame over which the trend is calculated or displayed. In some embodiments, the user may "zoom in" on a selected region of the trend. In some embodiments, the user may select which patterns are displayed and/or tracked. In some embodiments, various different displays may be included in the system to accommodate different needs of different users (such as a nurse, a physician, an anesthesiologist, and the like). Allowing the user to change the view of the waveform related features trend, may permit the user to toggle through the different levels of information for further evaluation of a condition. In further embodiments, the user interface may also allow the user to enter characteristic information for each patient. In some embodiments, the user interface may allow browsing capability that allows scrolling throughout the data over time. In some embodiments, the user interface may allow marking of events of interest for future evaluation.

Reference is now made to FIG. 1, which is a schematic representation of an exemplary display of a respiration waveform related feature trend and a representative waveform according to which the waveform related feature trend is determined. As shown in FIG. 1, the bottom panel displays a representative $CO_2$ waveform (10), as determined according to the measurement of $CO_2$ in exhaled breath ($EtCO_2$) of the patient being monitored. The representative waveform illustrated shows the concentration of $CO_2$ (mmHg) in exhaled breath over time (seconds). The time scale from the representative waveform is in the order of 5 to 10 seconds, as is common for the period of a breath. In the upper panel, a trend display (12) of the waveform related parameter (in this example, $EtCO_2$, measured in units of mmHg) is presented. The time scale of the trend display can be chosen at any time range, such as, for example, for 1-60 minutes (such as, for example, for 1, 5, 10, 20, 30 minutes), or for 1-24 hours (such as, for example, 1, 2, 6, 12 hours). Further, the user may zoom-in onto any section of the trend display in order to evaluate the fine details of the waveform related feature at any point of interest. The exemplary trend shown in FIG. 1 is of a two dimensional trend (in this example, $EtCO_2$ over time).

Figure 2:
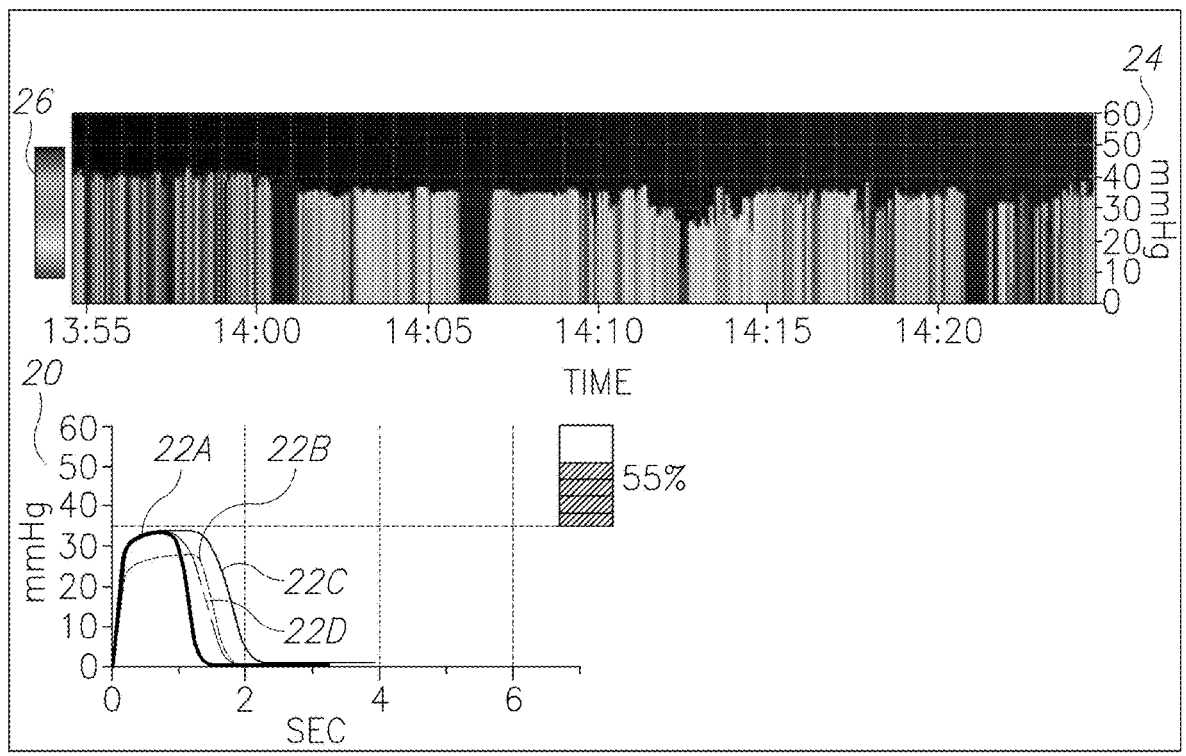
FIG. 2—a schematic representation of an exemplary display of trends of respiration waveform related features and representative waveforms, according to some embodiments.

Reference is now made to FIG. 2, which is a schematic representation of an exemplary display of trends of respiration waveform related features and representative waveforms. As shown in FIG. 2, the bottom panel (20) displays representative (recent) $CO_2$ waveforms (22C-D), as determined according to the measurement of $CO_2$ in exhaled breath ($EtCO_2$) of the patient being monitored. Further shown are baseline (reference) waveforms (22A-B) that may be selected by the health care provider. Such reference waveforms are used, for example, as a reference waveform prior to treatment, sedation, and the like. In the upper panel (24), a trend display of waveform related features is presented. The trend display in this example is the form of pillars (columns). The trend display shows several waveform related features (for example, $EtCO_2$ levels, breath width and calculated area under the curve of the waveform), wherein each of the features is represented by a different, distinct type of pillar. By different type of pillar it is meant that the pillars can be easily and readily be distinctly identified. For example, the pillars may have different colors, different shades, different shapes (for example, varying width/height of columns), different fill patterns (for example, empty, full, patterned), and the like. A code (such as a color code) correlating between the pillar and the feature it relates to may be indicated on the display, to allow the user to easily identify the various waveform related features. For example, a color may be representative of the level of area under the curve, the column (pillar) height may be representative of the $EtCO_2$ concentration and the width of the column may be representative of a measure of the breath width. As shown in FIG. 2, a color code (26, shown as gray scale code) is provided in order to interpret (represent) the scale of the depicted waveform related feature. In the example shown in FIG. 2, color code (26) is indicative of the level of area under the curve. The time period of the displayed trend can be chosen from a number of time periods (such as, for example, in the range of 1 to 60 minutes or 1 to 24 hours), and zooming in at any desired section is possible, in order to identify fine details, if so desired by the user. In some embodiments, the use of columns (pillars) to depict the waveform related features and not the waveform shapes themselves provide an easier, clearer and enhanced means that allows the health care provider to observe changes in the features and hence in the medical condition of the patient.

In some embodiments, additional waveform related parameters trends may be displayed, such that the trend of more than two features are simultaneously displayed in one trend display area, wherein each of the trends is easily distinguishable from the other. For example, additional waveform related feature may be the width of the exhalation period. For example, additional waveform related parameter may be the width of the inhalation period. Thus, in such example, the trend of four separate and distinct waveform related features may be simultaneously displayed in one trend display.

In some embodiments, the values of the trend of each of the waveform related features may be calculated from each individual waveform measured or calculated from a representative waveform.

Figure 3:
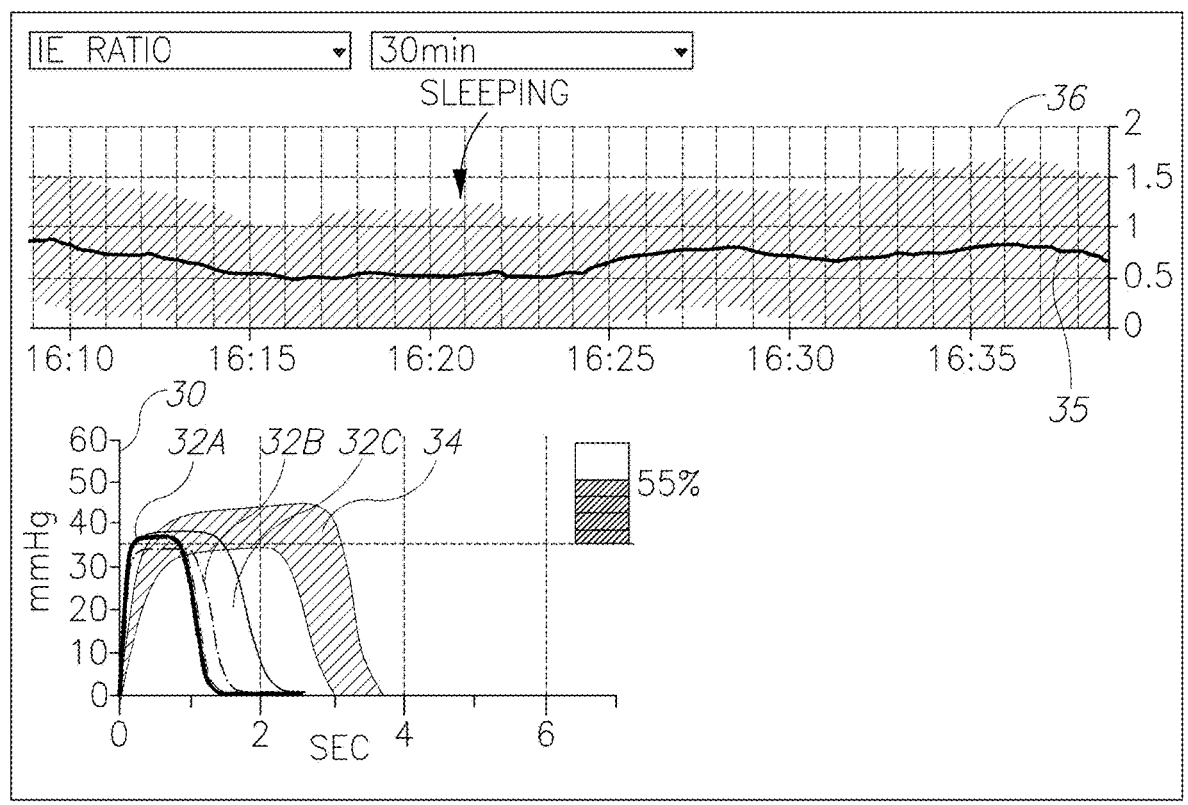
FIG. 3—a schematic representation of an exemplary display of trends of respiration waveform related features and representative waveforms, according to some embodiments.

Reference is now made to FIG. 3, which is a schematic representation of an exemplary display of trends of respiration waveform related features and representative waveforms. As shown in FIG. 3, the bottom panel (30) displays representative $CO_2$ waveform (32A), as determined according to the measurement of $CO_2$ in exhaled breath ($EtCO_2$) of the patient being monitored (mmHg/time(Sec)). Also shown are individual recent waveforms of recent measured breaths (32B-C). Further shown are reference waveform ranges (34, "Textbook"), of normal healthy patients, for providing a comparison means that may be used by the health care provider to simplify identification of pathological conditions. In the upper panel, a trend display (36) of waveform related features is presented. The trend display in this example is the form of a line (35) showing the average inhalation to exhalation ratio (I to E) over time, with the standard derivation depicted as shadowed area. The average I:E ratio and the standard deviation thereof may be calculated by various means, such as, for example, for an average of 2 or more breaths; over a given period of time; and the like. The average can be a running average or a continuous average. The values of the features may be calculated based on the individual waveform or the representative waveform. The trend display may further simultaneously display additional one or more features, such as, the respiration rate. The various trend of the features displayed may be visually distinguishable by varying thickness of the trend line, varying color of the trend line and the like. For example, the line may represent to I:E ratio and varying thickness or color of the line is representative of the respiration rate, or vice versa. Thus, in such example, several waveform related parameters, which physiologically relate to each other, may be simultaneously displayed in one graph. Further, in the example presented in FIG. 3, a health care provider can readily and relatively simply differentiate between, for example, systematic and erratic breathing pattern.

Figure 4:
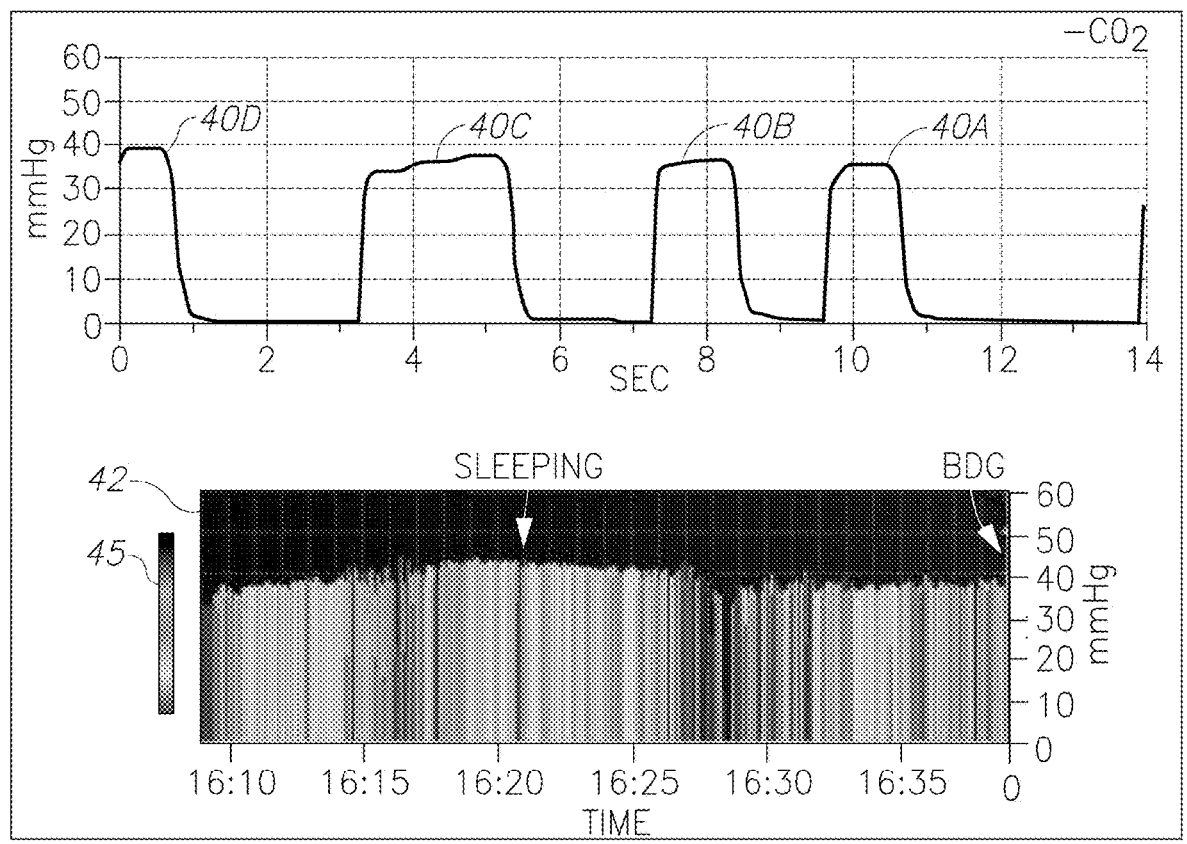
FIG. 4—a schematic representation of an exemplary display of trends of respiration waveform related features and representative waveforms, according to some embodiments.

Reference is now made to FIG. 4, which is a schematic representation of an exemplary display of trends of respiration waveform related features and representative waveforms. As shown in FIG. 4, the upper panel displays advancing instantaneous $CO_2$ waveforms (40A-D), as determined according to the measurement of $CO_2$ in exhaled breath ($EtCO_2$) of the patient being monitored (mmHg/time(Sec)). The trend information (42) is displayed in the lower panel. The trend information is shown in the form of columns, each representing a different waveform related feature, wherein the features in this example are related to the shape of the waveform. The columns are visually distinct (for example, by color, shade, width of column, shape of column, etc.). For example, the amplitude of the column represents the slope feature of the waveform and the color of the column represents the area under the curve. By this mode of display, the dominance or frequency extent of a waveform shape of interest is readily identifiable. A code (such as a color code (45)) correlating between the pillar and the feature it relates to may be indicated on the display, to allow the user to easily identify the various waveform related features. In addition, various additional medical parameters may further be depicted and presented. The additional medical parameters may be depicted manually (for example, by the health care provider) or automatically. In the example shown in FIG. 4, parameters such as "Sleeping" and "BDG" (which stands for blood gas) are depicted, to indicate their occurrence.

According to some embodiments, if in addition to the data from a capnograph (i.e. concentration of $CO_2$), additional medical information is provided, for example, regarding breath flow, additional useful information can be calculated and depicted. For example, if an integral of the flow pattern overtime is made with the CO2 concentration over time, a measure of the relative volume of expired CO2 can be calculated and depicted. The additional data can be used to evaluate changes or trends in minute ventilation. Trends of shallow breathing can also be noted, where rapid shallow breathing is used as a useful parameter and indicator during weaning process.

Figure 5A:
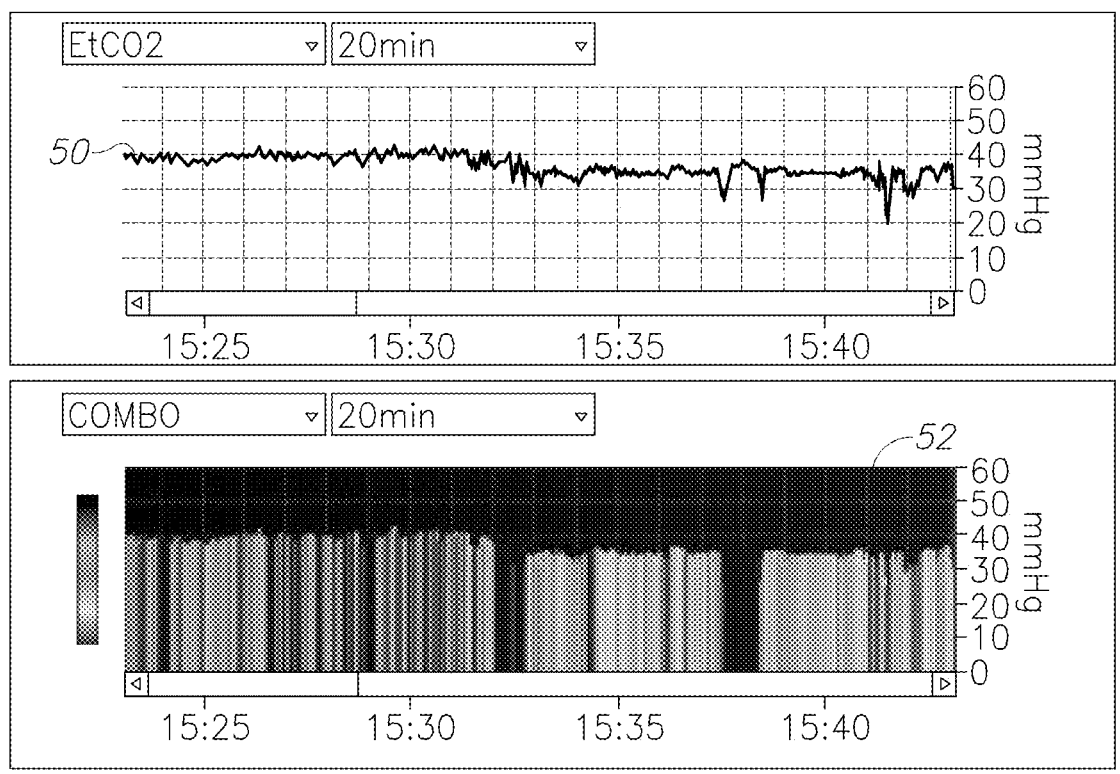
FIGS. 5A-B—schematic representations of exemplary displays of trends of respiration waveform related features that are shown in parallel, according to some embodiments.
Figure 5B:
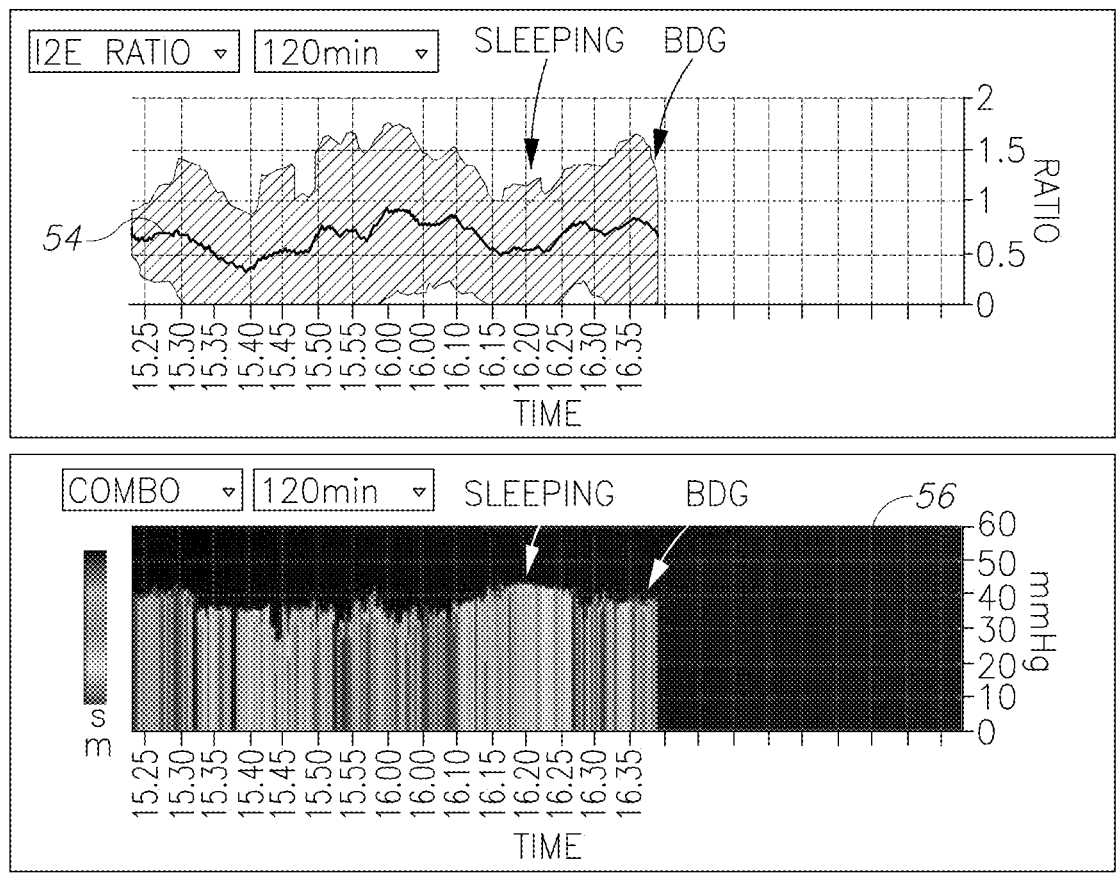

Reference is now made to FIGS. 5A-B, which are schematic representations of exemplary displays of trends of respiration waveform related features that can be shown in parallel. As shown in FIG. 5A, the upper panel shows the trend of the $EtCO_2$ feature over short period of time (in this example, 20 minutes), in the form of a line (50). The lower panel of FIG. 5A shows the trends of the EtCo2, area under the curve and the I:E ratio in the form of columns ((52), wherein the features are identified based on the color of the column) As shown in FIG. 5B, the upper panel presents the trend of the I:E ratio over a longer period of time (in this example, 120 minutes) in the form of a line (54). The lower panel of FIG. 5B shown the trends of the I:E ratio and the $EtCO_2$ in the form of columns ((56) with area under the curve defined by color. The two displays (FIG. 5A and FIG. 5B) may be simultaneously displayed in parallel in order to permit comparison of various features at similar times, and further allow identification of events that can be relates and shown together with multi pieces of information. In addition, various additional medical parameters may further be depicted and presented. The additional medical parameters may be depicted manually (for example, by the health care provider) or automatically. Such exemplary medical parameters (as shown in FIG. 5B), are "sleeping", and "BDG" (Blood Gas).

According to some embodiments, the trend display allows the option of "zooming in" on any time point(s) of the trend, to identify the actual parameter on which that trend was determined at the indicated time point(s). For example, when zooming in on the trend at a designated time point, the representative waveform which was observed at the same time point can be seen. According to further embodiments, scanning the trends too can be made simultaneous with the representative waveform. In some exemplary embodiments, additionally or alternatively to the presentation of an instantaneous moving waveform on the screen, a visualization of the lungs breathing (depicted, for example, by an animated cartoon of the lungs), whereby the rate of the breathing may be proportional to the present respiration rate (RR), and the size is relative to EtCO2, with optionally additional color code, indicative of the respiratory health of the patient.

It is understood by the skilled in the art that the processor of the system is configured to implement the method as essentially described herein.

In the description and claims of the application, each of the words "comprise" "include" and "have", and forms thereof, are not necessarily limited to members in a list with which the words may be associated.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

What is claimed is:

1. A medical monitoring system for identifying a trend of one or more waveform related features, the system comprising:
   a capnograph configured to measure a first medical parameter of a patient and to produce a train of moving waveforms of the first medical parameter over a time period;
   a processor configured to, in real time:
      analyze the set of the train of waveforms and one or more shape or scale factors thereof to provide a single waveform representative of one breath;
      identify and extract two or more features from the single waveform, wherein the two or more features relate to the set of the train of moving waveforms produced by the capnograph from a time range within the time period; and
      generate a first trend and a second trend of the two or more features based on the single waveform, wherein the first trend is associated with a first feature of the two or more features and the second trend is associated with a second feature of the two or more features that is different from the first feature; and
   a display configured to display the first trend and the second trend by displaying a shape corresponding to both the first trend and the second trend, wherein a first shape feature of the shape is selected based on the first trend and a second shape feature of the shape is selected based on the second trend.

2. The system of claim 1, wherein the first medical parameter of the patient is $CO_2$ in exhaled breath, and the second medical parameter is the patient's blood pressure, depth of sleep, or desaturation.

3. The system of claim 1, wherein the train of moving waveforms comprises $CO_2$ related waveforms.

4. The system of claim 1, wherein the two or more features are selected from shape factors and scale factors.

5. The system of claim 4, wherein the shape factors comprise up rising slope of a $CO_2$ waveform; the extent of the up-rising slope, the shape of the up-rising slope, the down-stroke slope of a $CO_2$ waveform, the extent of the down stroke slope, or the shape of the down stroke slope, or any combinations thereof.

6. The system of claim 4, wherein the scale factors comprise width of the waveform, time between sections of the waveform, or amplitude, or any combinations thereof.

7. The system of claim 1, wherein the two or more features comprises $EtCO_2$, changes in $EtCO_2$, a slope of the increase in the CO2 concentration, a change in a slope of the increase in the $CO_2$ concentration, time to rise to a predetermined percentage of a maximum value of $CO_2$ concentration, a change in time to rise to a predetermined percentage of a maximum value of $CO_2$ concentration, an angle of rise to a predetermined percentage of a maximum value of $CO_2$ concentration, a change in an angle of rise to a predetermined percentage of a maximum value of $CO_2$ concentration, breath to breath correlation, a change in breath to breath correlation, a $CO_2$ duty cycle, a change in $CO_2$ duty cycle, minute ventilation, or a change in minute ventilation, or any combinations thereof.

8. The system of claim 1, wherein the first trend and the second trend are indicative of the health condition of the patient.

9. The system of claim 1, wherein the shape is a column and wherein the first feature is a height or width of the column and the second feature is a color or fill of the column.

10. The system of claim 1, wherein the shape is a pillar or column and wherein the first feature is a height of the column and the second feature is a width of the column.

11. The system of claim 1, wherein the shape is a column and wherein the first feature is selected based on an EtCO2 concentration.

12. The system of claim 1, wherein the processor is configured to cause display of a second shape that corresponds to a second time range within the time period.

13. The system of claim 1, wherein the shape is displayed at a location corresponding to the time range on an x-axis of a plot and wherein a y-axis of the plot corresponds to units of the first trend.

14. The system of claim 1, wherein the processor is configured to produce the single waveform from analysis of one or more shape or scale factors of sequential waveforms in the set of the train of moving waveforms.

15. The system of claim 14, wherein the one or more shape or scale factors are derived from respective shape, dimension, rate or frequency, or reoccurrences in the sequential waveforms in the set of the train of waveforms.

16. The system of claim 1, wherein the display is configured to display the single waveform, the first trend, and the second trend.

17. The system of claim 1, wherein the display is configured to display one or more waveforms in the set of the train of moving waveforms and the single waveform.

* * * * *